US012005173B2

(12) United States Patent
Goodrich et al.

(10) Patent No.: US 12,005,173 B2
(45) Date of Patent: Jun. 11, 2024

(54) EXTRACORPOREAL CIRCUIT AND COLUMN DESIGN THEREFORE

(71) Applicant: IMMUTRIX THERAPEUTICS, INC., Rapid City, SD (US)

(72) Inventors: Todd Goodrich, Rapid City, SD (US); Ryan McGivern, Rapid City, SD (US); Rob Moyers, Rapid City, SD (US)

(73) Assignee: Immutrix Therapeutics, Inc., Rapid City, SD (US)

( * ) Notice: Subject to any disclaimer, the term of this patent is extended or adjusted under 35 U.S.C. 154(b) by 221 days.

(21) Appl. No.: 16/763,645

(22) PCT Filed: Nov. 16, 2018

(86) PCT No.: PCT/US2018/061508
§ 371 (c)(1),
(2) Date: May 13, 2020

(87) PCT Pub. No.: WO2019/099820
PCT Pub. Date: May 23, 2019

(65) Prior Publication Data
US 2020/0353151 A1    Nov. 12, 2020

Related U.S. Application Data

(60) Provisional application No. 62/587,090, filed on Nov. 16, 2017.

(51) Int. Cl.
*A61M 1/36* (2006.01)
*B01D 15/22* (2006.01)

(52) U.S. Cl.
CPC ........ *A61M 1/3621* (2013.01); *A61M 1/3626* (2013.01); *B01D 15/22* (2013.01); *A61M 2205/3331* (2013.01)

(58) Field of Classification Search
CPC .............. A61M 1/3621; A61M 1/3626; A61M 1/3679; A61M 2205/3331; A61M 2206/12; A61M 2206/16; B01D 15/22
See application file for complete search history.

(56) References Cited

U.S. PATENT DOCUMENTS 4,300,551 A * 11/1981 Kinney ............... A61M 1/3679
604/28
2011/0118683 A1   5/2011 Weston
(Continued)

FOREIGN PATENT DOCUMENTS

DE         19900731 A1   12/1999
EP         0318993 B1    6/1992
(Continued)

OTHER PUBLICATIONS

Filing receipt and specification for provisional patent application entitled "ExtraCorporeal Circuit and Column Design Therefore," by Todd Goodrich, et al., filed Nov. 16, 2017 as U.S. Appl. No. 62/587,090.
(Continued)

*Primary Examiner* — Dirk R Bass
(74) *Attorney, Agent, or Firm* — Barnes & Thornburg LLP; Jerry C. Harris, Jr.

(57) ABSTRACT

Systems and methods for the treatment of a bodily fluid, for example, using a cartridge that may include a cartridge body configured to retain an adsorptive material and an end segment configured to cover a first end of the cartridge body. The end segment may include a circular face comprising an outwardly truncated conical shape and defining an internal conical space, a cylindrical wall joined to a periphery of the circular face, and an inlet configured to provide fluid connection to a source of the bodily fluid. The inlet may be disposed tangential to the circular face at the cylindrical wall so as to direct bodily fluid entering the cartridge into the
(Continued)

internal conical space tangentially so as to decelerate the bodily fluid within the internal conical space prior to contact with the adsorptive material disposed within the cartridge body.

5 Claims, 9 Drawing Sheets

(56) References Cited

U.S. PATENT DOCUMENTS

| | | |
|---|---|---|
| 2012/0168384 A1 | 7/2012 | Anzai et al. |
| 2012/0209111 A1 | 8/2012 | Cowan et al. |
| 2015/0151037 A1 | 6/2015 | Nilsson |

FOREIGN PATENT DOCUMENTS

| | | |
|---|---|---|
| EP | 2042221 B1 | 5/2012 |
| WO | 2011040310 A1 | 2/2013 |
| WO | 2019099820 A1 | 5/2019 |

OTHER PUBLICATIONS

Foreign communication from a related counterpart application—International Search Report and Written Opinion, PCT/US2018/061508 dated Mar. 13, 2019, 14 pages.
European Patent Office, Supplementary Search Report issued in corresponding patent application, 9 pages, dated Jun. 14, 2021.
European Patent Office, International Search Report issued in PCT/US2018/061508, dated Mar. 13, 2019, 6 pages.

* cited by examiner

EXTRACORPOREAL CIRCUIT AND COLUMN DESIGN THEREFORE

CROSS-REFERENCE TO RELATED APPLICATIONS

This application is a filing under 35 U.S.C. 371 of International Application No. PCT/US2018/061508 filed Nov. 16, 2018, which claims priority to U.S. Provisional Patent Application No. 62/587,090 filed Nov. 16, 2017 by Todd Goodrich, et al. and entitled "Extracorporeal Circuit and Column Design Therefore" which is incorporated herein by reference as if reproduced in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Bodily fluids are liquids originating from inside the bodies of living humans. They include both fluids resident within the body and fluids that are excreted or secreted from the body. Bodily fluids serve as repositories for molecules that function as disease mediators or disease-related toxins during a pathophysiological event or function in the context of an autoimmune disorders. Attenuation of the activity associated with such molecules and, thus, downregulation of the resultant adverse events associated with levels of these molecules detrimental to a subject's physiological well-being, holds continuing potential for development into a multitude of treatment options.

Thus, an ongoing need exists for systems, apparatuses, and related methodologies for the selective removal of such molecules from bodily fluids.

SUMMARY

In an aspect, a cartridge for the treatment of a bodily fluid may comprise a cartridge body configured to retain an adsorptive material; and an end segment configured to cover a first end of the cartridge body, the end segment comprising a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body.

In an aspect, a method of removing one or more components present in bodily fluid to produce a decontaminated bodily fluid may comprise attaching a cartridge to an input for bodily fluid; attaching the cartridge to an output for a decontaminated bodily fluid from the cartridge; passing bodily fluid through the cartridge, wherein the cartridge comprises a cartridge body configured to retain an adsorptive material; and an end segment configured to cover a first end of the cartridge body, the end segment comprising a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body; and filtering one or more substances from the bodily fluid to produce the decontaminated bodily fluid.

In an aspect, a cartridge may comprise a cartridge body; an end segment configured to cover a first end of the cartridge body, the end segment comprising a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body; and an adsorptive material retained within the cartridge body by the at least one end segment.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Aspects of the disclosure include systems, apparatuses, and methods for contacting the bodily fluid of a subject with an apparatus configured for removal of one or more components, such as toxins or other small molecules, present in the bodily fluid to produce a decontaminated bodily fluid and returning at least a portion of the decontaminated bodily fluid to the subject. In some aspects, the bodily fluid may be blood or a blood component, for example, whole blood, red blood cells (i.e., erythrocytes), white blood cells (i.e., leukocytes), or combinations thereof. In one or more of the following aspects, the systems, apparatuses, and methods may be disclosed with reference to the treatment of blood or a blood component; nonetheless, the systems, apparatuses, and methods disclosed herein may, in other aspects, be likewise applicable to other bodily fluids. For example, additionally or alternatively, in various aspects the bodily fluid may comprise lymph, cerebrospinal fluid, bile, peritoneal fluid, serousal fluid, or combinations thereof.

Figure 1:
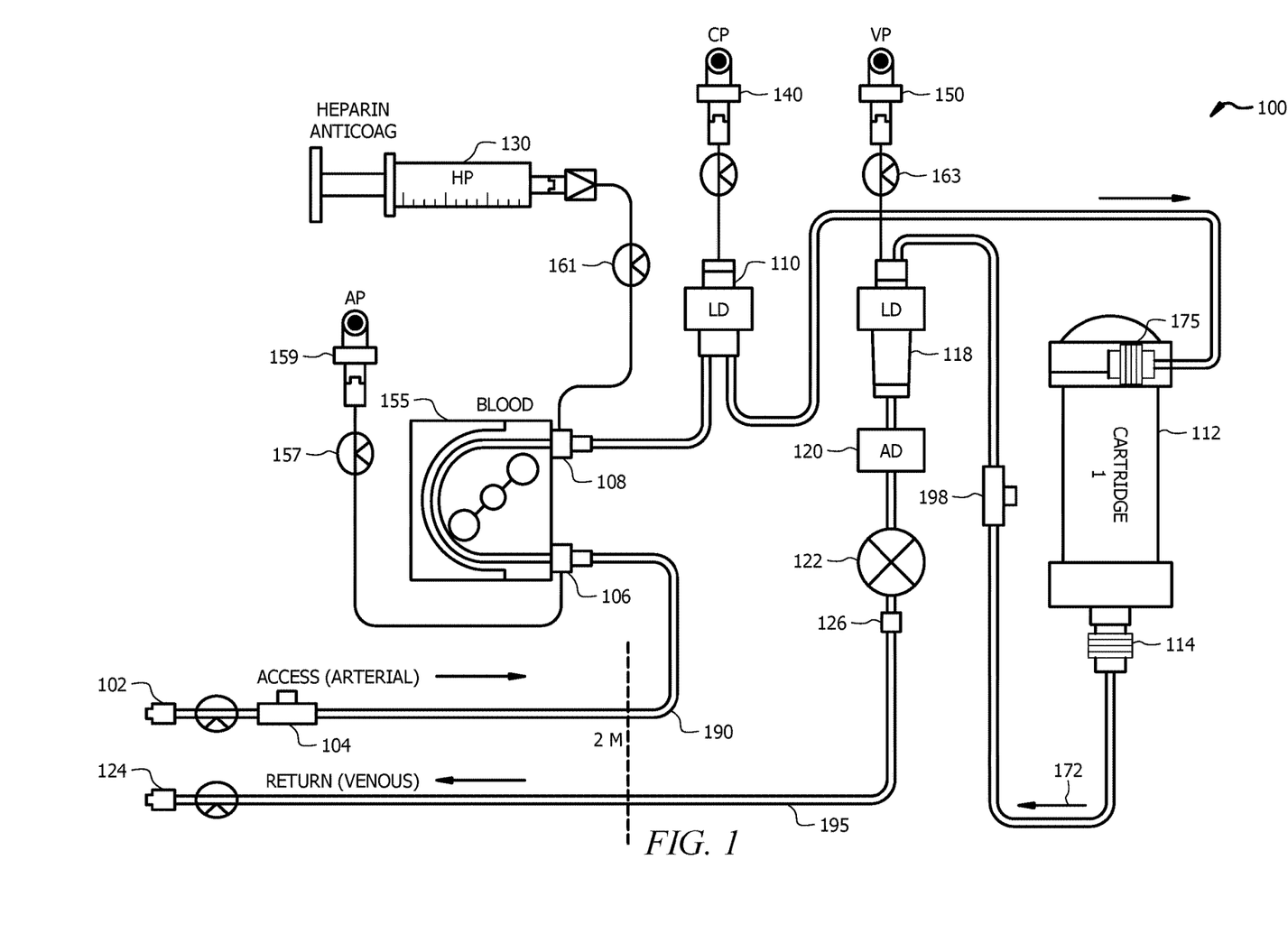
FIG. 1 illustrates a system including a cartridge for removing one or more components present in bodily fluid to produce a decontaminated bodily fluid according to an aspect of the disclosure.

An aspect of a system suitable for removal of one or more components from a bodily fluid is depicted in FIG. 1. In the aspect of FIG. 1, the system 100 comprises an inlet 102 that may be configured to receive blood-flow from the subject (e.g., a patient). For example, the inlet 102 may be configured to access an artery of the subject to provide blood flow from the subject via the inlet 102. In various aspects, access to blood flow may be attained through the jugular, subclavian, or femoral vein of the subject, such as with a double lumen catheter; other options for establishing blood flow from a subject include, for example and without limitation, chronic vascular accesses such as those used in hemodialysis, that are created by an earlier surgical procedure, for example native arteriovenous fistulas (native AVFs), arteriovenous shunts using graft material (AV graft), and tunneled double-lumen catheters. As a safety measure, in some aspects, the inlet 102 may include a plurality of electrodes (such as two to four electrodes), configured to sense and indicate disconnection of the inlet 102. An alternative aspect for detection of accidental disconnections is the use of a conductive blanket underneath the inlet 102. In such aspects, the presence of blood changes the conductivity of the blanket and sets off an alarm.

The inlet 102 may be in fluid communication with a pump 155 via a conduit 190. The conduit 190 may comprise a sampling infusion port 104, which may be configured to regulate access and fluid communication via the conduit 190. The pump 155 may regulate the communication of the subject's blood to the remainder of the system 100. The conduit 190 may comprise any suitable type or configuration and be comprised of material suitable for use in the methodologies disclosed herein. The conduit 190 is fluidly coupled to the pump 155 via a pump inlet port 106. The pressure at the pump inlet port 106 may be detected by an arterial pressure sensor 159 which may be selectively activated using a pinch clamp 157.

In some aspects, blood exiting the pump 155 via a pump outlet port may be contacted with an effective amount of anticoagulant, such as heparin, via a flowline connected to an anticoagulant source, illustrated as a heparin source 130 which may be selectively controlled via a pinch clamp 161. The heparinized blood may then be subsequently conveyed via outlet port 108 to a level detector 110 in signal communication with a cartridge pressure sensor 140 before entering a cartridge 112 via first end segment 175. The cartridge 112 may contain a therapeutic formulation comprising carbon, for treatment (e.g., removal of a component, such as a contaminant or toxin). Blood having been contacted with the therapeutic formulation present in cartridge 112 then exits the cartridge in a particular flow direction 172. Blood exiting from cartridge 112 through the outlet regulated by valve 114 may enter conduit 195 comprising a venous return 198 port.

The conduit 195 is fluidly coupled to a level detector 118 in signal communication with a venous pressure detector 150 which may be selectively activated using a pinch clamp 163. An air detector 120 may be positioned in-line with conduit 195 (along with a pinch clamp 122 and a transducer protector 126), which may then allow the blood to flow back to the subject via any suitable route such as and without limitation the jugular, subclavian or femoral vein, or another vasculature, via return 124.

In various aspects, system 100 may be generally configured such that the flow-rate of a bodily fluid (e.g., plasma, whole blood) through system 100 may be regulated to provide some user and/or process goal. For example, the flow-rate of blood through system 100 may range from about 1 mL/min to about 500 mL/min, or from about 25 mL/min to about 300 mL/min, or from about 25 mL/min.

In some aspect, the cartridge 112 may be configured to provide for sufficient contact between the bodily fluid (e.g., blood) being treated and a suitable treatment material contained therein. For example, referring to FIGS. 2 and 3, an aspect of a cartridge 200 suitably employed in the context of FIG. 1 and in the methods disclosed herein is depicted. Particularly, FIG. 2 illustrates a front view of the cartridge 200 and FIG. 3 illustrates a side view of the cartridge 200.

Figure 2:
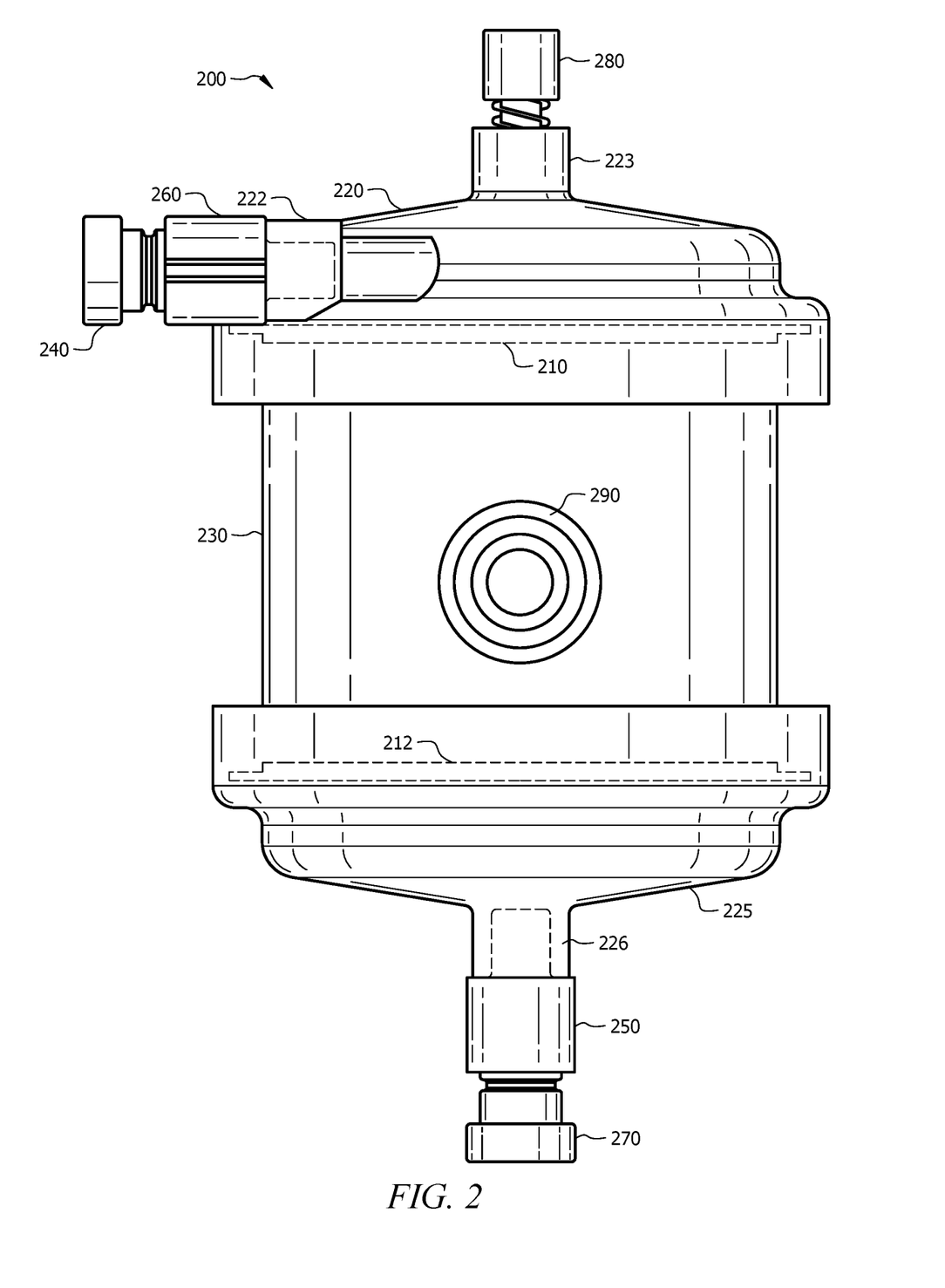
FIG. 2 illustrates a front view of a cartridge according to an aspect of the disclosure.
Figure 3:
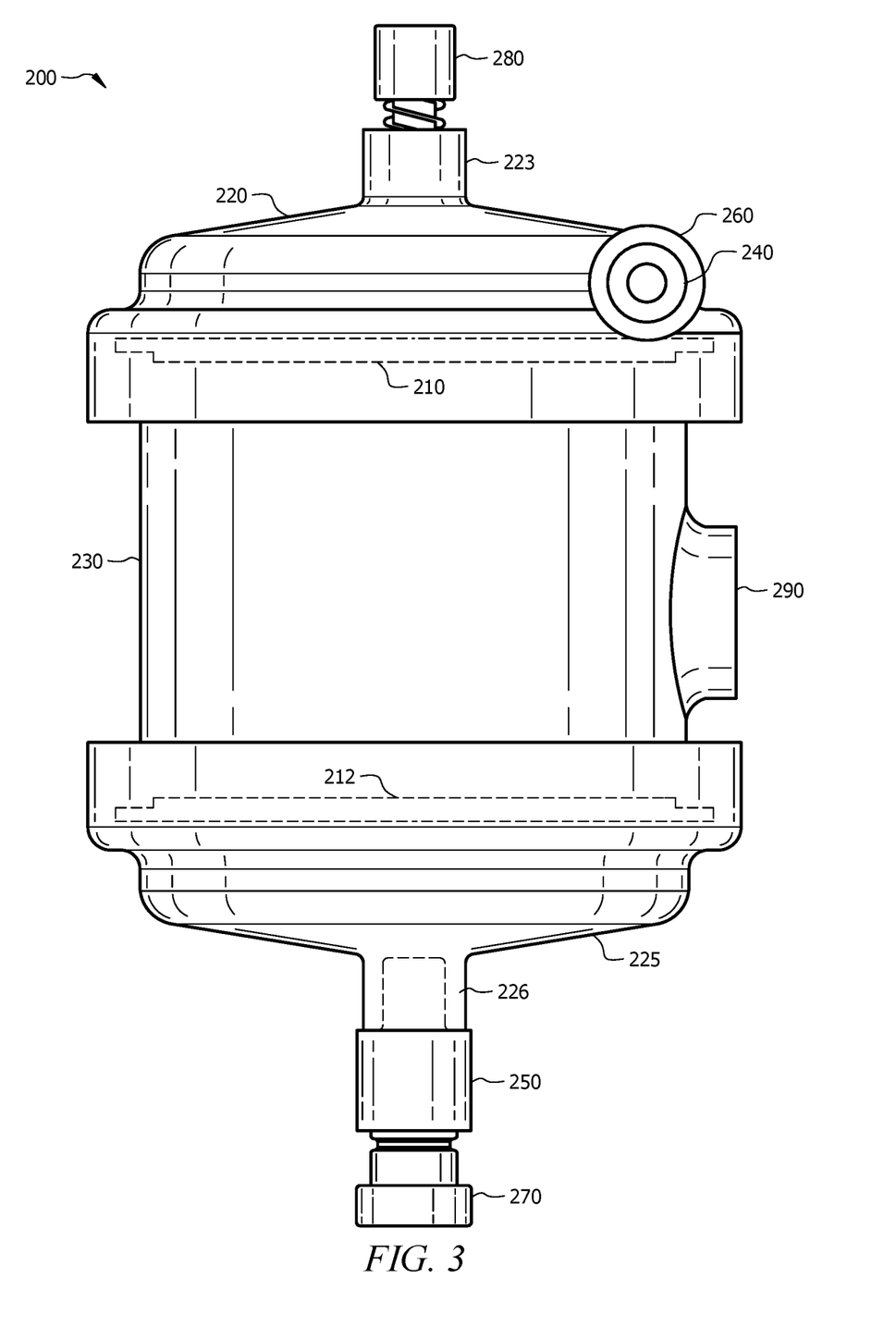
FIG. 3 illustrates a side view of a cartridge according to an aspect of the disclosure.

In the aspect of FIGS. 2 and 3, the cartridge 200 comprises a first end segment 220, a second end segment 225, and a cartridge body 230. In various aspects, one or more components forming the cartridge 200, for example, one or more of the first end segment 220, the second end segment 225, or the cartridge body 230 may be of any suitable material, for example, that is compatible with the processes and compositions with which the cartridge 200 is intended for use. Examples of such materials may include, but are not limited, polycarbonates such as high temperature polycarbonates, polysulfones, polyetherimides, autoclavable polypropylenes, polyethersulfones, and combinations thereof.

In some aspects, the configuration of the cartridge 200 disclosed herein, and more particularly, the configuration of the first end segment 220 disclosed herein, permits a bodily fluid, such as blood, to enter the cartridge body 230 in such a way as to decrease the chaotic, turbulent nature of the flow of the bodily fluid prior to the bodily fluid interacting with a treatment material disposed in the cartridge body 230. In some aspects, this reduction in chaotic, turbulent flows prior to interaction with the treatment material (within the cartridge body 230) may be effective to reduce any detrimental impact associated with subjecting the whole blood or plasma to a chromatographic cartridge, as will be disclosed herein.

In some aspects, the cartridge body 230 generally comprises a hollow, cylindrical structure. In various aspects, the cartridge body 230 may comprise a single, integral structure or, may comprise two or more operably-joined components. The cartridge body 230 may generally define an interior space, for example, in which the treatment material may be disposed, as will be disclosed herein. In some aspects, the first end segment 220 and the second end segment 225 may substantially enclose cartridge body 230, for example, so as to form a substantially sealed internal space. In some aspects, the first end segment 220 and/or the second end segment 225 may comprise components that are separate from the cartridge body and are configured to be engaged with the cartridge body 230. For example, in some aspects, the first end segment 220 (e.g., a first cap or cover) and/or the second end segment 225 (e.g., a second cap or cover) may be configured to engage with the cartridge body 230 via a threaded interface so as to secure the first end segment 220 and/or the second end segment 225 to the cartridge body 230. Additionally or alternatively, in some aspects, the components of the cartridge 200 may be attached to one another via a suitable adhesive. For example, as an additional or alternative example, the first end segment 220 and/or the second end segment 225 may be attached to the cartridge body 230 via one or more layers of adhesive. In other aspects, the two or more components of the cartridge 200 may be integral with each other. For example, in some aspects, the first end segment 220 and/or the second end segment 225 may be integral (e.g., formed as a part of) to the cartridge body 230.

In some aspects, the cartridge 200 may comprise one or more screen assemblies, for example, a first screen assembly 210 that may be disposed between the first end segment 220 and the cartridge body 230 and/or a second screen assembly 212 disposed between the second end segment 225 and the cartridge body 230.

In some aspects, the first end segment 220 comprises a first inlet 222 disposed within the first end segment 220 and generally configured to direct a flow of bodily fluids into the cartridge 200, particularly, into the first end segment 220. In some aspects, and as will be disclosed herein, the first inlet 222 may be configured to direct fluid flow into the first end segment in a direction generally tangential to first end segment 220. In some aspects, the first inlet 222 may be configured to engage a luer fitting 260, which may be configured to receive a luer plug 240, for example, so as to be fluidly coupled to a conduit (e.g., conduit 190, in the context of FIG. 1).

In some aspects, the first end segment 220 may further comprise a second inlet 223. The second inlet 223 may be generally configured to direct fluid into the first end segment 220 in a direction generally parallel to a longitudinal axis of the cartridge 200 (e.g., at the center of the first end segment 220). In some aspect, the second inlet 223 may be configured to receive a luer fitting, such as a luer cap 280. In various aspects, the second inlet 223 may provide an addition route of fluid flow into the first end segment 220 (e.g., for delivery of a therapeutic compound or a second bodily fluid), a route of fluid flow out of the first end segment 220 (e.g., to recycle a portion of the flow flow), or a port for monitoring or relieving pressure within the cartridge 200.

In some aspects, the second end segment may comprise an outlet 226. The outlet 226 may be generally configured to direct fluid out of the cartridge 200. In some aspects, the outlet 226 may be configured to engage a luer return fitting 250, which may be configured to receive a luer plug 270, for example, so as to be fluidly coupled to a conduit (e.g., conduit 195, in the context of FIG. 1).

In some aspects, the cartridge body 230 may also comprise a plug 290, for example, so as to permit access the interior of the cartridge body 230.

Figure 4:
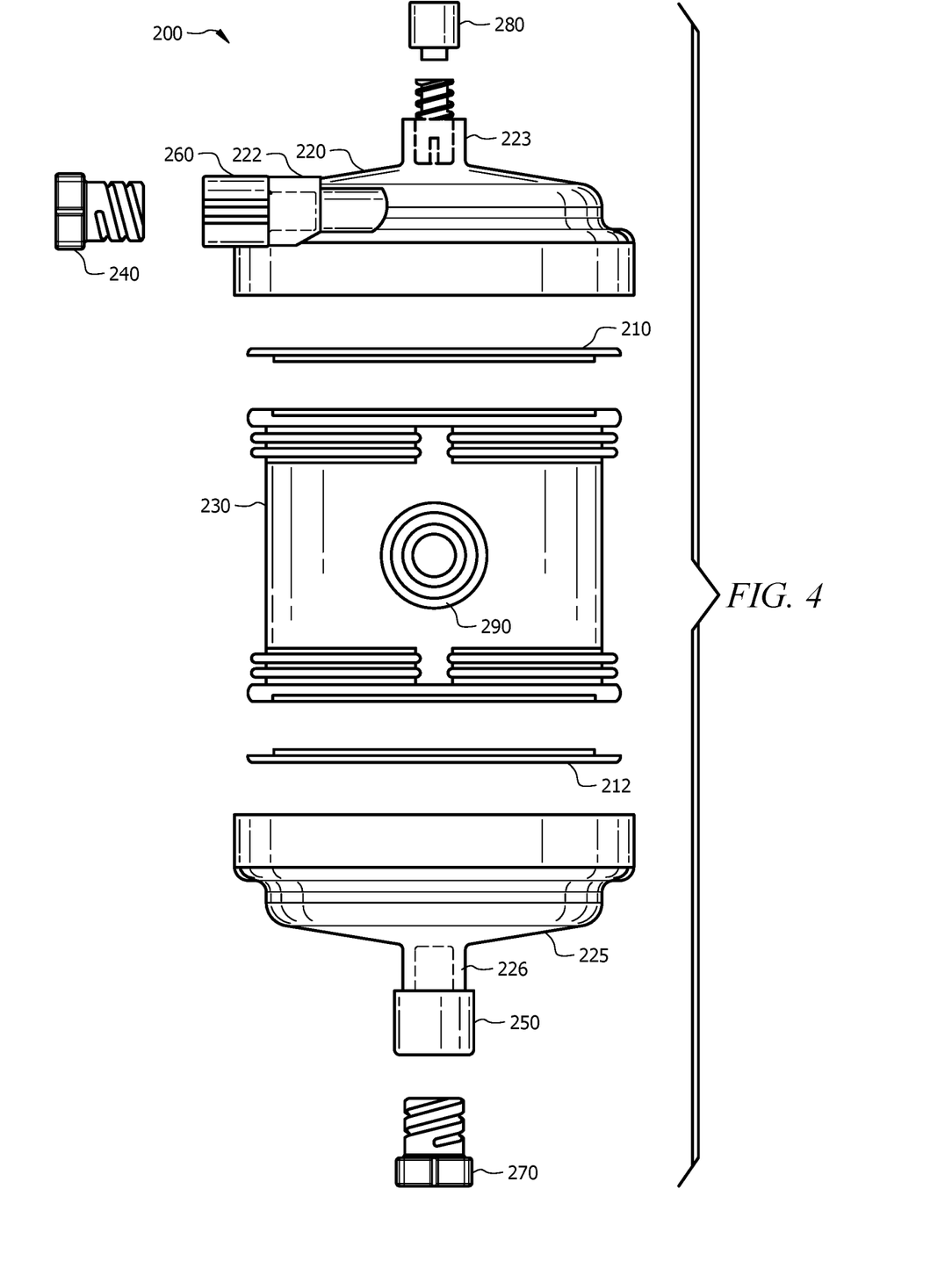
FIG. 4 illustrates an exploded view of a cartridge according to an aspect of the disclosure.

Referring to FIG. 4, an exploded view of the cartridge 200 is illustrated. In some aspects, the components of the cartridge 200 may be engaged with one another via any suitable interface, for example, a threaded connection, a compression interface, an adhesive, or the like. For example, the screen assembly 210 may be held in place between the first end segment 220 and cartridge body 230 upon fitment of the first end segment 220 to the cartridge body 230 or via one or more layers of adhesive. Similarly, the screen assembly 212 may be held in place between the second end segment 225 and the cartridge body 230 upon fitment of the second end segment 225 to the cartridge body 230 or via one or more layers of adhesive.

Figure 5:
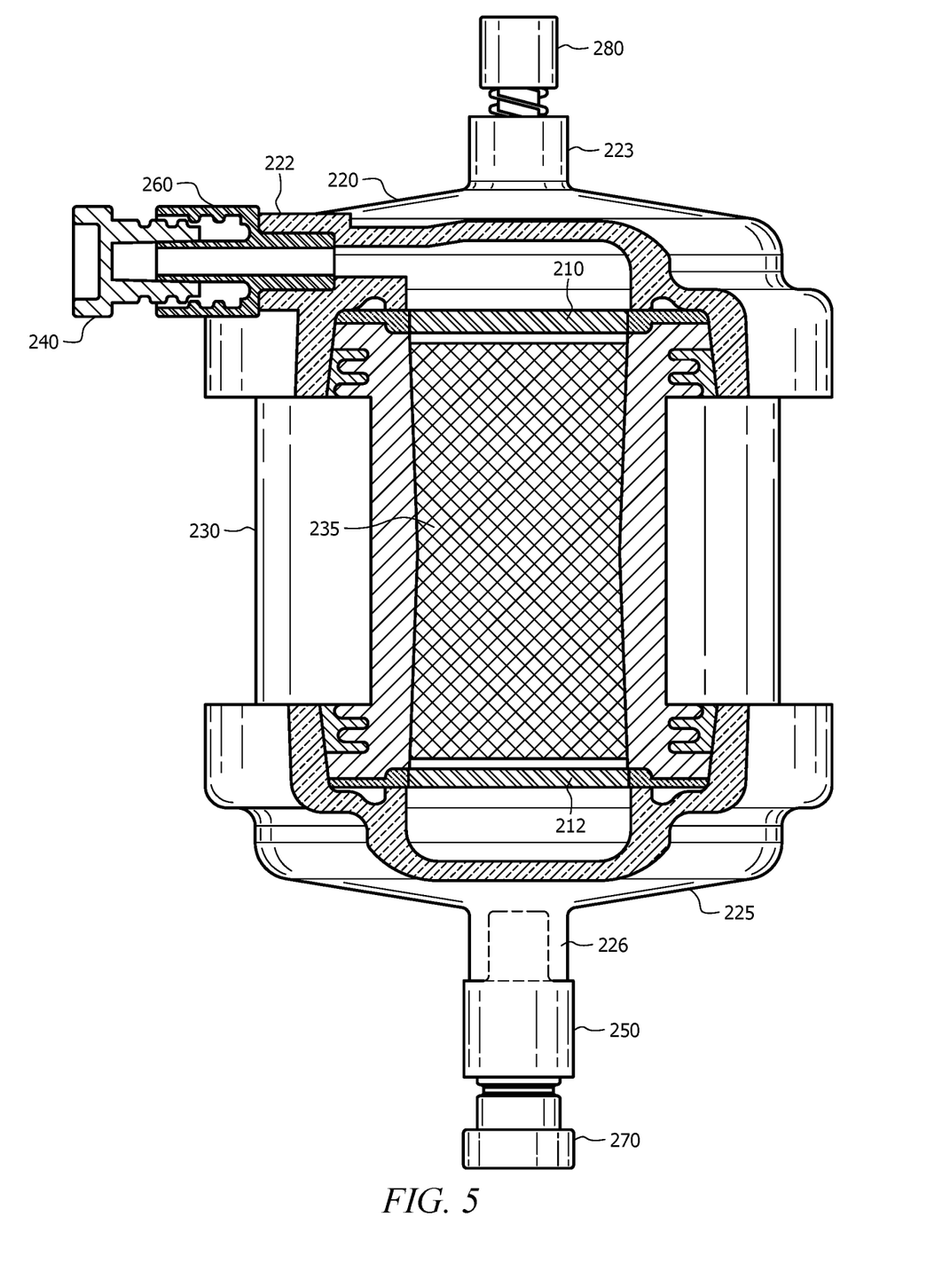
FIG. 5 illustrates a cross-sectional view of a cartridge according to an aspect of the disclosure.

Referring to FIG. 5, a cross-sectional view of the cartridge 200 is illustrated. The planar cross-section of FIG. 5 is in a plane extending through the center of the first inlet 222 of the first end segment 220 (as well as the luer plug 240 and luer fitting 260). In some aspects, and as illustrated in FIG. 5, the cartridge 200 may also comprise a treatment material, for example, an adsorptive material 235 retained within the cartridge body 230 by the one or more screen assemblies 210 and 212.

In some aspects, the adsorptive material comprises synthetic carbon particles (SCP), for example, activated carbon (e.g., activated carbon beads, and/or medical grade carbon), containing micro-, meso-, and/or macro-pores formed from porous phenolic resins. As used herein, the term "micropore" refers to a pore with diameter<2 nm, as measured by nitrogen adsorption and mercury porosimetry methods and as defined by IUPAC. As used herein, the term "mesopore" refers to pores with diameter from ca. 2 nm to ca. 50 nm, as measured by nitrogen adsorption and mercury porosimetry methods and as defined by IUPAC. As used herein, the term "micropore" refers to pores with diameters larger than 50 nm, as measured by nitrogen adsorption and mercury porosimetry methods and as defined by IUPAC.

A SCP suitable for use in the present disclosure may have any shape compatible with the compositions and methodologies disclosed herein. For example the shape of the SCP may be that of an irregular granule, a low angularity shape, spherical (e.g., bead), pellet, minilith, monolith, or the like. For simplicity, the present disclosure may refer to the use of beads of the SCB however it is to be understood the SCP may be of any suitable shape. The SCPs may be formed using any suitable methodology to results in a material having the properties disclosed herein. In an exemplary method for the formation of an SCP, a precursor resin formulation is used which comprises a large proportion of pore former, e.g. 250 parts ethylene glycol or other pore former to 100 parts of resin-forming components.

Herein a mesoporous resin may be formed by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g. ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart meso-or macroporosity to the resin (e.g. at least 120 parts by weight of the pore former being used to dissolve 100 parts by weight of the total resin forming components, i.e. nucleophilic component plus electrophilic component), and it is removed from the porous resin after condensation by cascade washing with water or by vacuum drying. The resulting resin may be carbonised by heating in an inert atmosphere to a temperature of at least 600° C. to give a material having a bimodal distribution of pores, the pore structure as estimated by nitrogen adsorption porosimetry comprising micropores and mesopores or macropores. The value for the differential of pore volume with respect to the logarithm of pore radius (dV/d log R) for the mesopores is greater than 0.2 for at least some values of pore size in the range 20-500 Å. The mesoporous carbon may have a BET surface area of 250-800 $m^2/g$ without activation. The mesoporous carbon may be activated by heating it at high temperature in the presence of carbon dioxide, steam, or a mixture thereof, for example, by heating it in carbon dioxide at above 800° C., or it may be activated by heating it in air at above 400° C. It may then have surface areas of up to 2,000 $m^2/g$ and even higher, such as, 1,000-2,000 m²/g. As used herein the term "BET surface area" is determined by the Brunauer, Emmett, and Teller (BET) method according to ASTM D1993-91, see also ASTM D6556-04.

Figure 6:
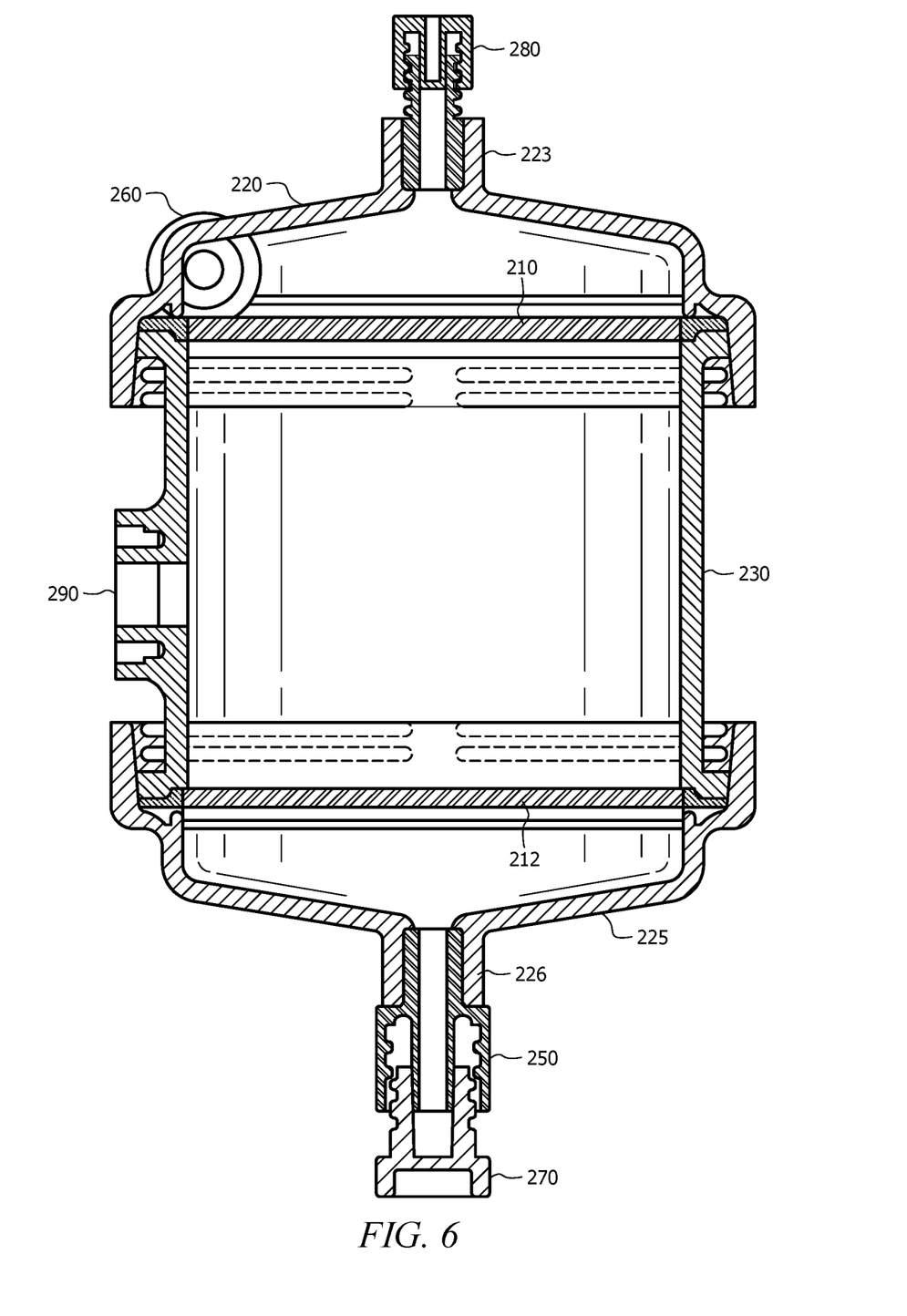
FIG. 6 illustrates another cross-sectional view of a cartridge according to an aspect of the disclosure.

In some aspects, the placement of the first inlet 222 may be configured to direct the bodily fluid in a particular flow pattern, for example, to control the rate and/or direction in which the bodily fluid passes through the screen assembly 210 and into the cartridge body 230, before contacting the adsorptive material 235. For example, FIG. 6 illustrates a cross-sectional view of the assembled cartridge 220, where the plane of the cross section extends through the center of the port 290. FIG. 6 illustrates the assembled cartridge 220 (for example, without the adsorptive material disposed within the cartridge body 230). As shown in FIGS. 5 and 6, and as disclosed more particularly with respect to the following figures, the first inlet 222 is disposed in the first end segment 220 such that a bodily fluid received via the first inlet 222 is directed into the first end segment 220 tangential thereto.

Figure 7:
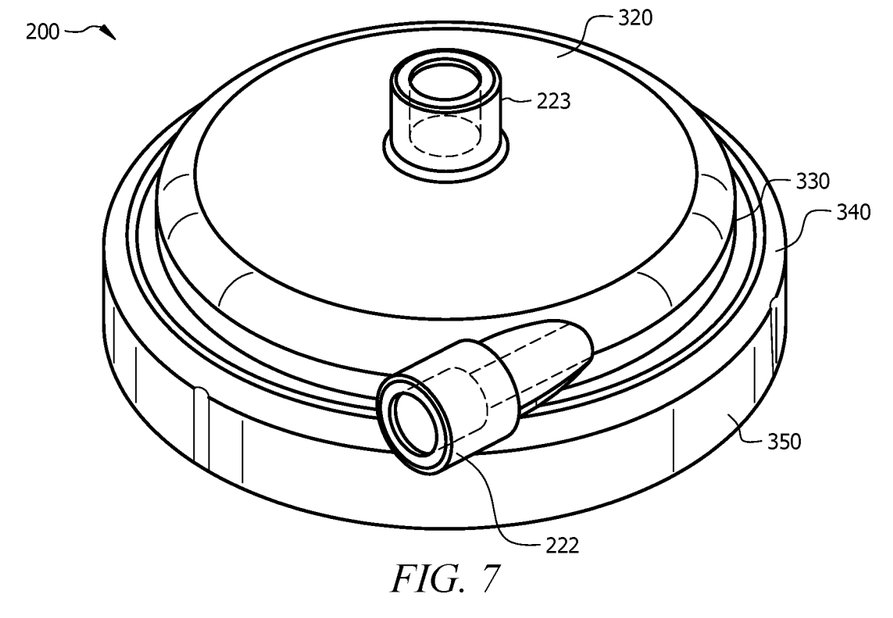
FIG. 7 illustrates a perspective view of an end segment of a cartridge according to an aspect of the disclosure.
Figure 8:
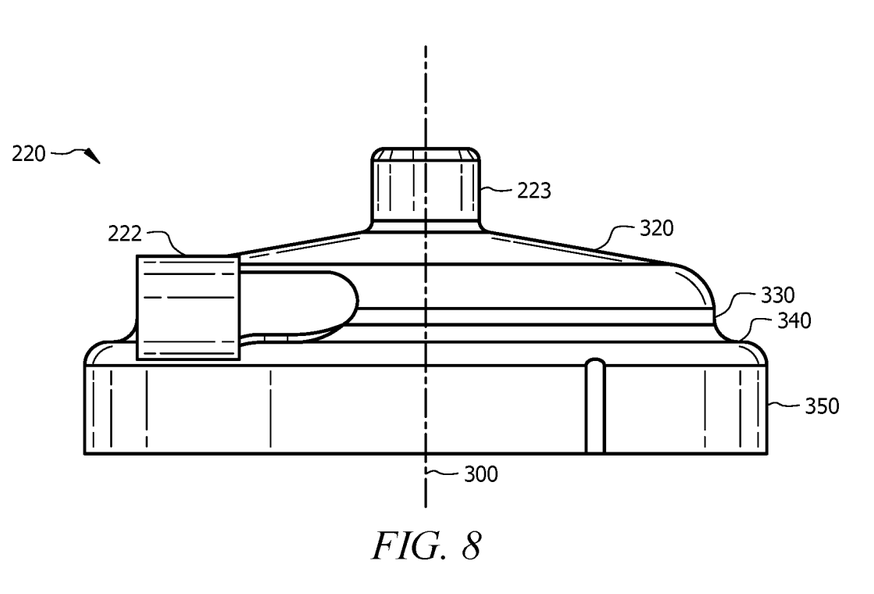
FIG. 8 illustrates a side view of an end segment of a cartridge according to an aspect of the disclosure.

More particularly, referring to FIGS. 7 and 8, the first end segment 220 comprises the first inlet 222 positioned tangentially to a circular face 320 of the first end segment 220. The first end segment 220 may also comprise the second inlet 223 positioned in the center of the circular face 320 (e.g., at the conical point or apex) of the first end segment 220. The second inlet 223 may extend generally perpendicular to the exterior of the first end segment 220.

The circular face 320 of the first end segment 220 may comprise an outwardly truncated conical shape and defining an internal conical space. The circular face 320 may be connected to or joined to a cylindrical wall 330, which may extend generally parallel to a central longitudinal axis 300 of the first end segment 220. As shown, the first inlet 222 may be disposed tangential to the circular face 320 and at the cylindrical wall 330 so as to direct the flow of a bodily fluid entering the first end segment 220 via the first inlet 222 into the internal conical space tangentially.

The first end segment 220 may also comprise a ledge 340 joined to the cylindrical wall 330. The ledge 340 may extend within a plane generally perpendicular to the central axis 300 of the first end segment 220. The ledge 340 may be configured to fit against one or more elements of the cartridge to which the first end segment 220 is attached, e.g., a screen assembly and/or cartridge body (as shown above). The first end segment 220 may also comprise a second cylindrical wall 350 joined to the periphery of the ledge 340, where the second cylindrical wall 350 also extends generally parallel to a central axis 300 of the first end segment 220. In some aspects, the second cylindrical wall 350 may comprise one or more attachment elements configured to attach the first end segment 220 to a cartridge, e.g., to the cartridge body 230. In some aspects, the cylindrical wall 350 may be configured to fit over a portion of the cartridge body 230. For example, the ledge 340 and/or cylindrical wall 350 may attach to the cartridge body 230 via adhesive or a threaded interface.

Figure 9:
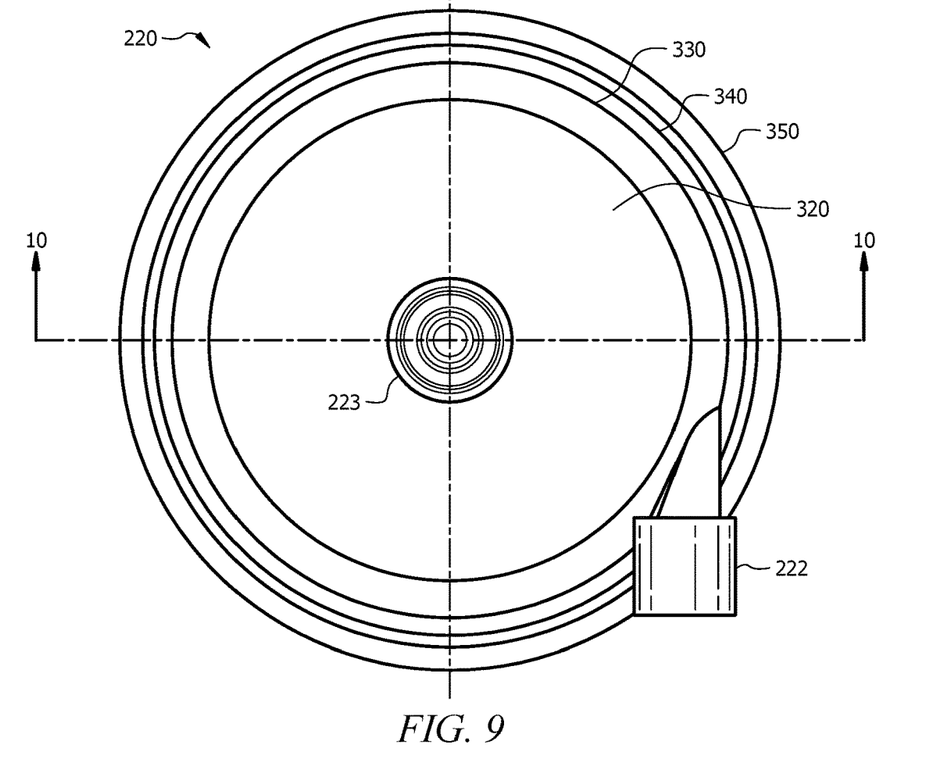
FIG. 9 illustrates a top view of an end segment of a cartridge according to an aspect of the disclosure.
Figure 10:
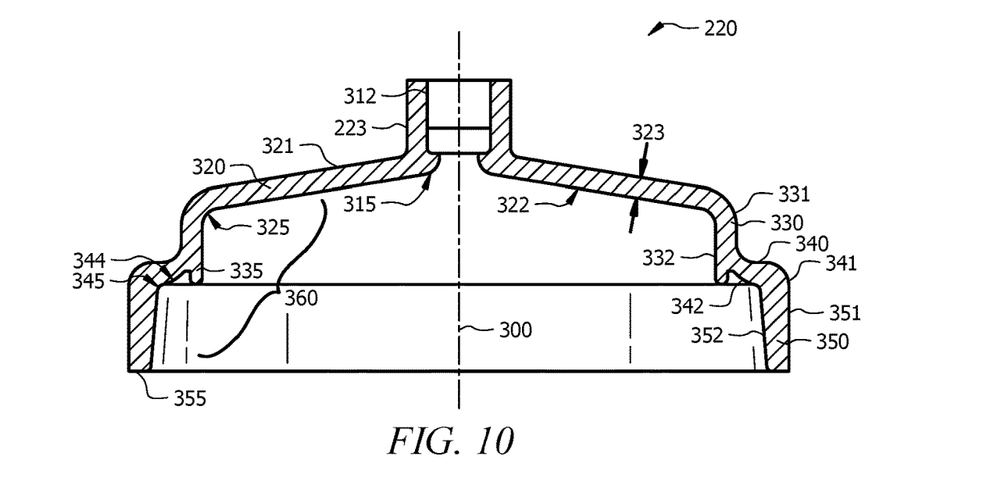
FIG. 10 illustrates a cross-sectional view of an end segment of a cartridge according to an aspect of the disclosure.

FIG. 9 illustrates a top view of the first end segment 220 and FIG. 10 illustrates a cross-sectional view of the first end segment 220, wherein the cross-section is through the second inlet 223 of the first end segment 220. In some aspects, the second inlet 223 may comprise an interior surface or profile 312 configured to receive another element of a cartridge, e.g., a luer cap. The circular face 320 may comprise an exterior surface 321 and an interior surface 322. The first cylindrical wall 330 may comprise an exterior surface 331 and an interior surface 332. The ledge 340 may comprise an exterior surface 341 and an interior surface 342. The second cylindrical wall 350 may comprise an exterior surface 351 and an interior surface 352. The circular face 320 may also comprise a thickness 323.

In some aspects, the circular face 320, first cylindrical wall 330, ledge 340, and second cylindrical wall 350 may collectively define an interior surface 360, which in whole or in part, is generally configured to direct fluid flow within the first end segment 220. The interior surface 360 may be defined by the interior surface 322 of the circular face 320, the interior surface 332 of the first cylindrical wall 330, the interior surface 342 of the ledge 340, and/or the interior surface 352 of the second cylindrical wall 352.

In some aspects, the interior surface 360 may be defined by a curved surface 315 connecting the interior surface 312 of the second inlet 223 to the interior surface 322 of the circular face 320. In some aspects, the interior surface 360 may include a curved surface 325 connecting the interior surface 322 of the circular face 320 to the interior surface 332 of the first cylindrical wall 330. In some aspects, the interior surface 360 may be defined by a curved surface or protrusion 335 connecting the interior surface 332 of the first cylindrical wall 330 to the interior surface 342 of the ledge 340. In some aspects, the interior surface 360 may be defined by a curved surface 344 within the interior surface 342 of the ledge 340. In some aspects, the interior surface 360 may be defined by a curved surface 345 connecting the interior surface 342 of the ledge 340 to the interior surface 352 of the second cylindrical wall 350. In some aspects, the second cylindrical wall 350 may comprise an edge surface 355, which may define a bottom plane of the first end segment 220 that is perpendicular to the central axis 300 of the first end segment 220.

Figure 11:
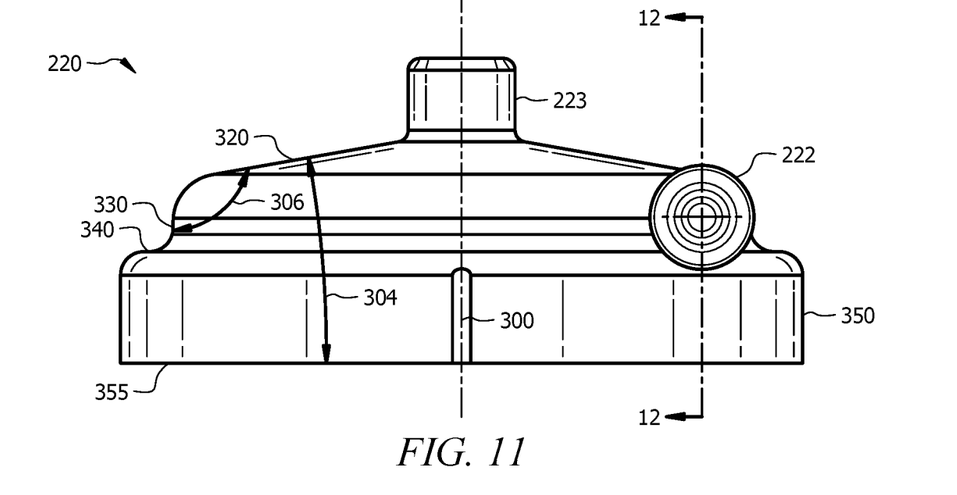
FIG. 11 illustrates another side view of an end segment of a cartridge according to an aspect of the disclosure.

FIG. 11 illustrates another side view of the first end segment 220. In some aspects, an angle of inclination 304 of the circular face 320 with respect to a plane (e.g., the bottom surface 355) perpendicular to a longitudinal axis 300 of the cartridge may be between about 5° to about 30°. In some aspects, an angle of inclination 304 of the circular face 320 with respect to a plane (e.g., the bottom surface 355) perpendicular to a longitudinal axis 300 of the cartridge may be between about 7° to about 15°. In some aspects, the cylindrical wall 330 may be joined to the circular face 320 at an angle 306 of about 95° to about 120°.

Figure 12:
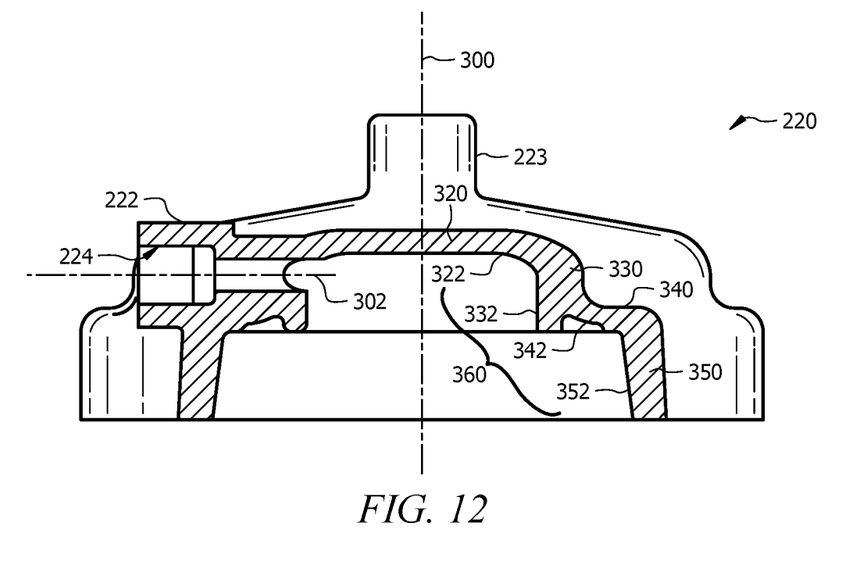
FIG. 12 illustrates another cross-sectional view of an end segment of a cartridge according to an aspect of the disclosure.

FIG. 12 illustrates another cross-sectional view of the first end segment 220, where the cross-section is through the first inlet 222. In some aspects, the first inlet 222 may comprise a central axis 302 that is perpendicular to a longitudinal axis 300 of the first end segment 220. In some aspects, the first inlet 222 may comprise an interior surface or profile 224, for example, configured to receive a luer fitting and/or luer plug (as described above). In some aspects, the second cylindrical surface may comprise ridges or discontinuities and an internal concentric concave raised surface 351 with ridges or discontinuities that may be configured to seal the first end segment 220 to a cartridge (e.g., a cartridge body).

In some aspects, the placement of the first inlet 222 with respect to the first end segment 220 yield a flow of the bodily fluid into the first end segment 220 in a direction tangential to the first end segment, for example, such that the bodily fluid flow radially (e.g., in a spiral pattern) as it enters the cartridge 200. Not intending to be bound by theory, this flow pattern may subject the bodily fluid to relatively less chaotic, turbulent behavior in comparison to an axial flow, for example, by increasing the available path length within the first end segment before passing through the adsorptive material 235. For example, the partially conical shape of the first end segment 220 along with the tangential position of the first inlet 222 allows the incoming bodily fluid to decelerate (e.g., decrease in fluid velocity) and lose energy before passing through the screen assembly 210 and into the adsorptive material 235.

The first end segment 220 comprising the first inlet 222 may provide a smoother entry into the cartridge body 230 through radial flow dynamics. The flow dynamic created by the first end segment 220 may provide a gentler entry into the cartridge body 230 with the tangential inlet 222 which may be configured to align the incoming blood (or bodily fluid) with the radial flow dynamics present in the interior of the first end segment 220 and the cartridge body 230, thus more closely mimicking laminar flow. The longer pathway created by this direction of the bodily fluid flow may reduce the fluid velocity and may minimize turbulence of the fluid flow before passing through the screen assembly 210. In some aspects, the first end segment 220 may be configured to decelerate the bodily fluid from the rate at which the bodily fluid enters the first inlet 222 by between about 5% and 90% of the inlet rate. In some aspects, the first end segment 220 may be configured to decelerate the bodily fluid from the rate at which the bodily fluid enters the first inlet 222 by between about 5% and 50% of the inlet rate. In some aspects, the first end segment 220 may be configured to decelerate the bodily fluid from the rate at which the bodily fluid enters the first inlet 222 by between about 5% and 25% of the inlet rate.

Conversely, in a cartridge lacking an end segment have a tangential inlet (e.g., the first end segment 220 having the first inlet 222, as disclosed herein), blood axially entering an enclosed space (e.g., the cartridge body 230) filled with adsorptive material contained by screen mesh barriers may exhibit sufficient velocity and turbulence as to cause platelet activation and/or fibrinogen deposition both on the screen mesh and the contained adsorptive material. Additionally, the resultant increase in differential pressure may contribute to decreased flow and adsorption kinetics along with negative hematologic changes. When passing blood though the cartridge 200 in the manner described above, platelet activation and fibrinogen deposition may be substantially reduced.

As such, in some aspects, the presently disclosed cartridge 200 may be effective to mitigate problems associated with other cartridge designs in use in extracorporeal circuits, and may be particularly advantageously employed while the bodily fluid is blood or a component of blood, such as by yielding a relative reduction in (i) platelet loss, (ii) white blood cell loss, (iii) platelet aggregation, (iv) pressure increase across the cartridge when in operation, (v) incidence of thrombocytopenia, (vi) incidence of leukopenia, (vii) microemboli, (viii) blood debris, or combinations of these.

Some aspects of the disclosure may comprise methods for removing one or more components present in bodily fluid to produce a decontaminated bodily fluid. An exemplary method may comprise attaching a cartridge (e.g., a cartridge 200 as described above) to an input for bodily fluid. In some aspects, the input for bodily fluid may be an arterial flow of blood from a patient. The method may comprise attaching the cartridge to an output a decontaminated bodily fluid from the cartridge. In some aspects, the output for decontaminated bodily fluid may comprise a venous flow of blood to a patient. The method may comprise passing bodily fluid through the cartridge, wherein the cartridge comprises a cartridge body configured to retain an adsorptive material, and an end segment configured to cover a first end of the cartridge body. The end segment of the cartridge may comprise a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body. The method may further comprise filtering one or more substances from the bodily fluid (e.g., by an adsorptive material contained within the cartridge) to produce the decontaminated bodily fluid.

In some aspects, the method may comprise establishing a fluid connection between a pump and at least one of the input or the output of the cartridge. In some aspects, the method may comprise pumping, via the pump, the bodily fluid through the cartridge. In some aspects, the method may comprise measuring, via level detector, the cartridge pressure. In some aspects, the method may comprise drawing the bodily fluid from a subject (e.g., via an arterial access flow line); and allowing the decontaminated bodily fluid to flow back to the subject (e.g., via a venous return flow line).

Having described various devices and methods herein, exemplary aspects or aspects can include, but are not limited to:

In a first aspect, a cartridge for the treatment of a bodily fluid may comprise a cartridge body configured to retain an adsorptive material; and an end segment configured to cover a first end of the cartridge body, the end segment comprising a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body.

A second aspect can include the cartridge of the first aspect, further comprising an inlet luer fitting affixed to the inlet configured to connect the cartridge to a source of bodily fluid.

A third aspect can include the cartridge of the first or second aspects, wherein the end segment comprises a cap configured for attachment to the cartridge body.

A fourth aspect can include the cartridge of the third aspect, further comprising an adhesive configured to attach and seal the at least one cap to the cartridge body.

A fifth aspect can include the cartridge of any of the first through fourth aspects, further comprising one or more screen assemblies positioned between the end segment and the cartridge body.

A sixth aspect can include the cartridge of any of the first through fifth aspects, wherein the end segment further comprises an inlet disposed in an axial center of the circular face.

A seventh aspect can include the cartridge of any of the first through sixth aspects, wherein the circular face comprises an angle of inclination of from about 5° to about 30° with respect to a plane perpendicular to a longitudinal axis of the cartridge.

An eighth aspect can include the cartridge of any of the first through seventh aspects, wherein the circular face comprises an angle of inclination of from about 7° to about 15° with respect to a plane perpendicular to a longitudinal axis of the cartridge.

A ninth aspect can include the cartridge of any of the first through eighth aspects, wherein the cylindrical wall is joined to the circular face at an angle of from 95° to about 120°.

In a tenth aspect, a method of removing one or more components present in bodily fluid to produce a decontaminated bodily fluid may comprise attaching a cartridge to an input for bodily fluid; attaching the cartridge to an output for a decontaminated bodily fluid from the cartridge; passing bodily fluid through the cartridge, wherein the cartridge comprises a cartridge body configured to retain an adsorptive material; and an end segment configured to cover a first end of the cartridge body, the end segment comprising a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body; and filtering one or more substances from the bodily fluid to produce the decontaminated bodily fluid.

An eleventh aspect can include the method of the tenth aspect, further comprising establishing a fluid connection between a pump and at least one of the input or the output of the cartridge.

A twelfth aspect can include the method of the eleventh aspect, further comprising pumping, via the pump, the bodily fluid through the cartridge.

A thirteenth aspect can include the method of any of the tenth through twelfth aspects, further comprising measuring, via level detector, the cartridge pressure.

A fourteenth aspect can include the method of any of the tenth through thirteenth aspects, further comprising drawing the bodily fluid from a subject; and allowing the decontaminated bodily fluid to flow back to the subject.

In a fifteenth aspect, a cartridge may comprise a cartridge body; an end segment configured to cover a first end of the cartridge body, the end segment comprising a circular face comprising an outwardly truncated conical shape and defining an internal conical space; a cylindrical wall joined to a periphery of the circular face; and an inlet configured to provide fluid connection to a source of the bodily fluid, wherein the inlet is disposed tangential to the circular face at the cylindrical wall so as to direct bodily fluid entering the cartridge into the internal conical space tangentially so as to decelerate the bodily fluid within the internal conical space prior to contact with the adsorptive material disposed within the cartridge body; and an adsorptive material retained within the cartridge body by the at least one end segment.

A sixteenth aspect can include the cartridge of the fifteenth aspect, further comprising at least one inlet port disposed in the center of the at least one end segment that extends vertically to the exterior of the at least one end segment.

A seventeenth aspect can include the cartridge of the fifteenth or sixteenth aspect, further comprising an inlet luer fitting affixed to the inlet configured to connect the cartridge to a source of bodily fluid.

An eighteenth aspect can include the cartridge of the seventeenth aspect, further comprising a luer plug configured to attach to the inlet luer fitting.

A nineteenth aspect can include the cartridge of any of the fifteenth through eighteenth aspects, wherein the end segment comprises a cap configured for attachment to the cartridge body.

A twentieth aspect can include the cartridge of the nineteenth aspect, further comprising an adhesive configured to attach and seal the at least one cap to the cartridge body.

What is claimed is:

1. A method of removing one or more components present in bodily fluid to produce a decontaminated bodily fluid, the method comprising:
    attaching a cartridge to an input for bodily fluid;
    attaching the cartridge to an output for a decontaminated bodily fluid from the cartridge;
    passing bodily fluid through the cartridge, wherein the cartridge comprises:
    a cartridge body configured to retain an adsorptive material; and
    an end segment configured to cover a first end of the cartridge body, the end segment comprising:
        a circular face comprising an outwardly truncated conical shape and defining an internal conical space;
        a cylindrical wall joined to a periphery of the circular face; and
        an inlet configured to provide fluid connection to a source of the bodily fluid, wherein the inlet comprises a central axis that is perpendicular to a longitudinal axis of the end segment, wherein the inlet is (1) disposed tangential to the circular face at the cylindrical wall so as to (i) direct bodily fluid entering the cartridge into the internal conical space tangentially so as to decelerate the bodily fluid within the internal conical space prior to contact with the adsorptive material disposed within the cartridge body, and (ii) cause the bodily fluid to enter the cartridge substantially perpendicular to a flow direction of the bodily fluid through the adsorptive material and (2) configured to utilize gravity to assist the bodily fluid with contacting the adsorptive material; and
    filtering one or more substances from the bodily fluid to produce the decontaminated bodily fluid.

2. The method of claim 1, further comprising establishing a fluid connection between a pump and at least one of the input or the output of the cartridge.

3. The method of claim 2, further comprising pumping, via the pump, the bodily fluid through the cartridge.

4. The method of claim 1, further comprising measuring, via level detector, the cartridge pressure.

5. The method of claim 1, further comprising drawing the bodily fluid from a subject; and allowing the decontaminated bodily fluid to flow back to the subject.

* * * * *